US00PP35794P2

(12) United States Plant Patent
Zlesak

(10) Patent No.: US PP35,794 P2
(45) Date of Patent: May 7, 2024

(54) ***PHYSOCARPUS* PLANT NAMED 'AUNTIE B'**

(50) Latin Name: *Physocarpus opulifolius*
Varietal Denomination: Auntie B

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 18/445,375

(22) Filed: Aug. 8, 2023

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson

(57) ABSTRACT

'Auntie B' is a new and distinct cultivar of *Physocarpus opulifolius* plant having an upright, mounded, dense plant habit; compact overall plant size; strong branching characteristics; small orange-red emerging foliage that matures to purple; short internode length; resistance to powdery mildew; corymbs of small blush-white flowers that are produced in late spring into early summer and reliably and abundantly again on vigorous current season stem terminals from mid-summer into fall; coral-pink to red follicle color when in full sun for about a month after fertilization; and ability to root and grow vigorously from softwood and semi-hardwood stem cuttings.

9 Drawing Sheets

Latin name of the plant claimed: *Physocarpus opulifolius*.
Variety denomination: 'Auntie B'.

BACKGROUND OF THE INVENTION

The present invention relates to a new and distinct cultivar of *Physocarpus opulifolius* and will be referred to hereafter by its cultivar name, 'Auntie B'. *Physocarpus opulifolius* (commonly known as ninebark, common ninebark, Atlantic ninebark, and Eastern ninebark) is a deciduous shrub grown primarily for landscape use. The key objective within the *Physocarpus opulifolius* breeding program I initiated in St. Paul, Minn. in 2001 and now continue in River Falls, Wisc. has been to develop new *Physocarpus opulifolius* cultivars that are compact growing, well-branched, healthy, rebloom freely, and possess colorful foliage for landscape use. One specific goal has been to develop a cultivar with the orange-red to golden new foliage color that matures to purple on a compact, well branched plant like *Physocarpus opulifolius* 'ZLEBic5' (disclosed in U.S. Plant Pat. No. 31,235), but with the ability to more reliably rebloom throughout the summer and fall.

'Auntie B' originated as a unique seedling within what can be described as an $F_2$ population. Open-pollinated seed was collected off of 'ZLEBic5' (cross of *Physocarpus opulifolius* 'Donna May' (disclosed in U.S. Plant Pat. No. 22,634) as the female parent and *Physocarpus opulifolius* 'Dart's Gold' (not patented)). 'ZLEBic5' (maternal parent of 'Auntie B') was growing in isolation with eleven of its full siblings. Ninebark displays self-incompatibility, and it is expected that 'Auntie B' is a cross between 'ZLEBic5' and a compatible full sibling of 'ZLEBic5' (one of the eleven full siblings growing close by was 'ZLEYel2' (disclosed in U.S. Plant Pat. No. 31,198) and the remaining ten full siblings are not patented). The pollination that led to the population of seedlings from which 'Auntie B' was identified occurred in spring 2016. The seeds of this population germinated during the winter of 2016/2017 indoors under florescent lights in River Falls, Wisc. During the first growing season, seedlings with attractive foliage color, relatively compact growth habit, and powdery mildew resistance were retained and in August 2017 planted in an outdoor ground bed in River Falls, Wisc. 'Auntie B' stood out as a highly desirable genotype among this seedling population as it matured, in part due to it having very reliable rebloom that is stronger than 'ZLEBic5'. 'Auntie B' was first asexually propagated using semi-hardwood and softwood stem cuttings in River Falls, Wisc. during the summer of 2019. I have found that the characteristics of 'Auntie B' are stable and true to type over successive generations of vegetative propagation.

'Auntie B' is unique relative to other ninebark seedlings in my breeding program and all cultivars I am aware of because of its warm orange-red to golden new growth that matures to purple, its compact and very well-branched plant habit, and it having the most abundant and reliable rebloom of any ninebark genotype I am aware of. 'Auntie B' has attractive blush-white flowers that are abundant and attractive against the colorful foliage. As follicles develop, they are a coral-pink to red color for about a month and provide ornamental value. 'Auntie B' displays reliable repeat flowering on the terminals of current season stems from mid-summer into fall. Natural branching without pruning due to terminal inflorescences in summer leads to an abundance of new stems with colorful tips and adds to the ornamental appearance of 'Auntie B'. Natural branching also contributes to a full and symmetrical plant without as much need for pruning, streamlining maintenance during both the production phase and in the final landscape.

SUMMARY OF THE INVENTION

The primary objective of the breeding goal was substantially achieved, along with other desirable improvements, as evidenced by the following unique combination of characteristics that are outstanding in the new variety and that distinguish it from other ninebark in my breeding program as well as from all other cultivars of *Physocarpus opulifolius* of which I am aware:

1. Upright, mounded, dense plant habit;
2. Compact overall plant size;
3. Strong branching characteristics;
4. Small orange-red emerging foliage that matures to purple;
5. Short internode length;
6. Resistance to powdery mildew;
7. Corymbs of small blush-white flowers that are produced in late spring into early summer and reliably and abundantly again on vigorous current season stem terminals from mid-summer into fall;
8. Coral-pink to red follicle color when in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls, Wisc. shows that the foregoing and all other characteristics and distinctions come true to form and are established and transmitted through succeeding asexual propagations.

Comparison with Parents

'Auntie B' is a seedling of 'ZLEBic5' as the maternal parent crossed with full siblings of 'ZLEBic5' ('ZLEBic5' and its full siblings are hybrids of 'Donna May' as the female parent and 'Dart's Gold' as the male parent). 'Auntie B' is similar to 'ZLEBic5' in that they both have relatively small leaves that emerge a warm orange-red to golden color before they mature to purple. Both 'Auntie B' and 'ZLEBic5' have similar foliage size along with abundant branching. 'Auntie B' has more reliable and abundant rebloom later in the growing season on terminals of vigorous new stems than 'ZLEBic5', slightly more branching, and a slightly smaller mature plant size. The exact genotype that served as the male parent of 'Auntie B' is unknown. The full siblings of 'ZLEBic5' growing adjacent to 'ZLEBic5' are the expected males of the seedling population leading to 'Auntie B'. The full siblings of 'ZLEBic5' varied for foliage color (golden-green, purple, and the combination of golden-green with purple), branching propensity on current season's growth without pruning, and mature plant size. 'Auntie B' differs from the eleven potential male parents in that 'Auntie B' has a smaller mature plant size and more abundant and reliable rebloom than them all.

Comparison of 'Auntie B' with a Similar Cultivar

A *Physocarpus opulifolius* cultivar that shares similarity with 'Auntie B' is 'ZLENatalie' (disclosed in U.S. Plant Pat. No. 34,244). New growth of both cultivars is a warm orange-red to golden color that matures to purple. The new growth of 'Auntie B' tends to more often have a golden hue and 'ZLENatalie' more often have more of an orange-red color. 'Auntie B' and 'ZLENatalie' both have relatively small leaves, small flowers, abundant natural branching on current season's growth without pruning, good tolerance to powdery mildew, and a relatively compact mature plant size compared to the majority of ninebark cultivars. 'Auntie B' has more reliable and abundant rebloom in mid-summer into fall and a more compact mature plant size than 'ZLENatalie'.

BRIEF DESCRIPTION OF THE DRAWINGS

The accompanying colored photographs illustrate key features of 'Auntie B'. Photographs show the colors as true as it is reasonably possible to obtain with colored reproductions of this type. Colors in the photographs may differ slightly from the color values cited in the detailed botanical description, which accurately describe the colors of 'Auntie B'. The plant of 'Auntie B' photographed is the ortet in its seventh growing season (2023) in a garden bed in River Falls, Wisc.

DETAILED BOTANICAL DESCRIPTION

Figure 1:
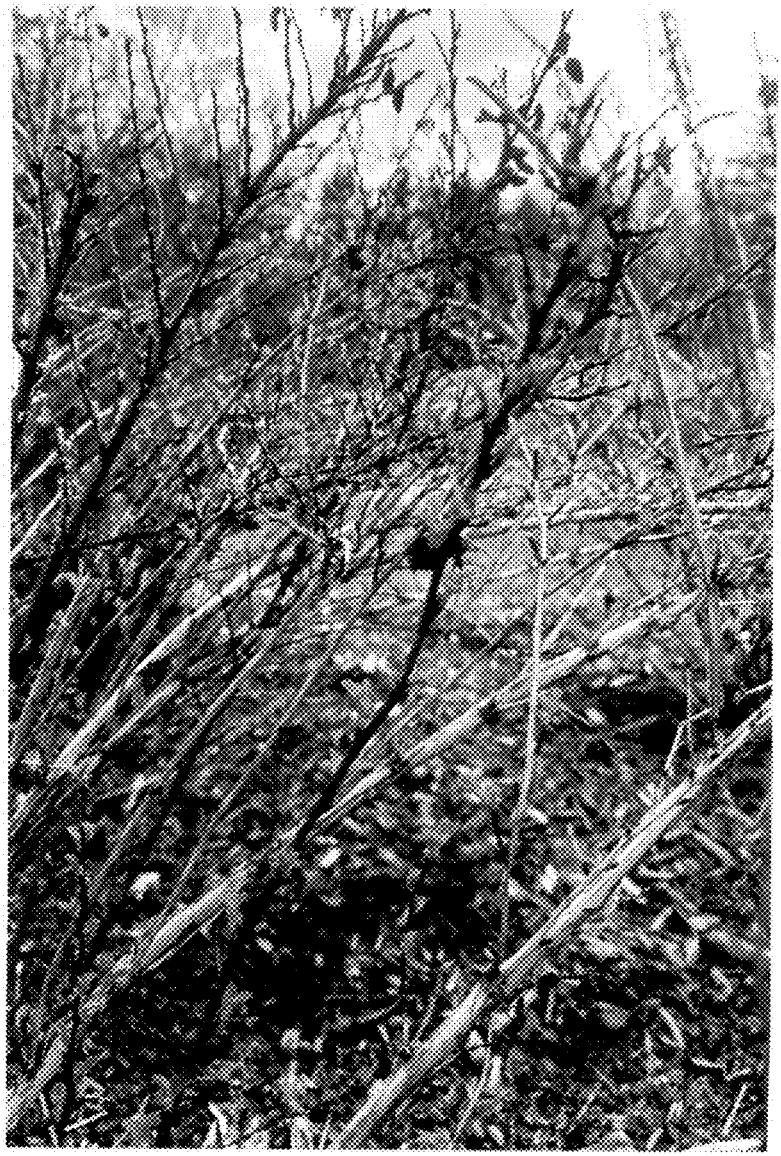
FIG. 1 illustrates emerging foliage in April.
Figure 2:
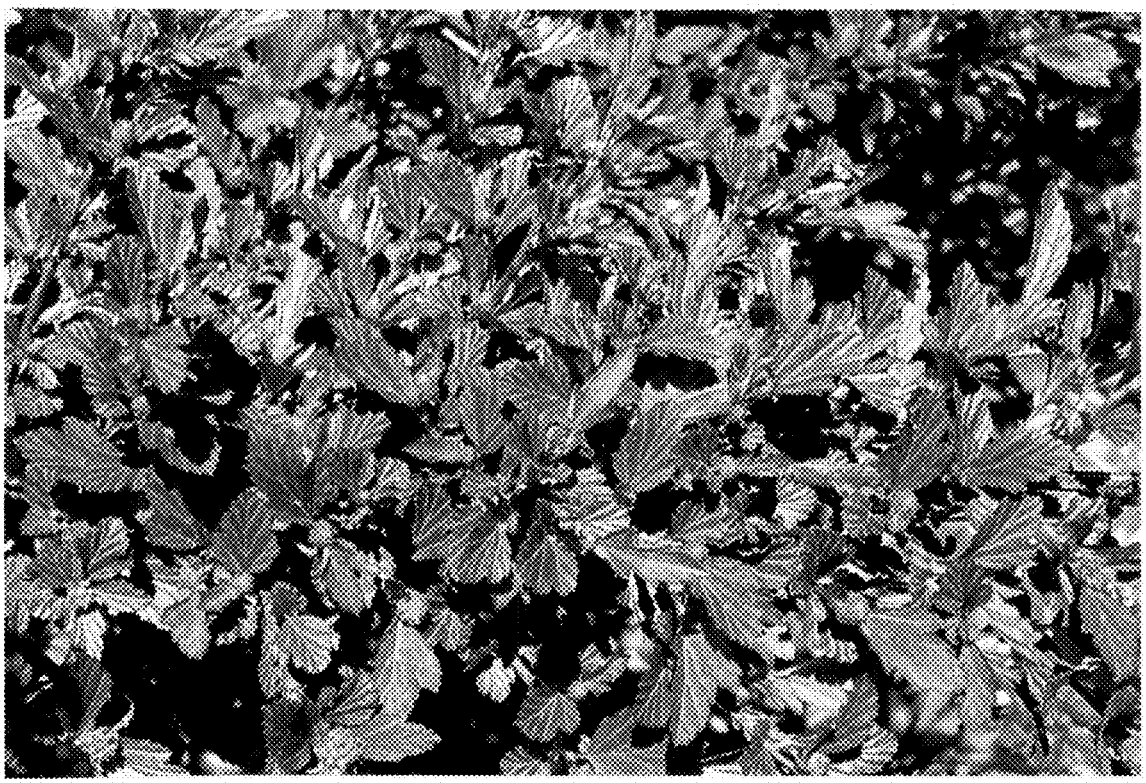
FIG. 2 illustrates expanding foliage and developing inflorescences in early May.
Figure 3:
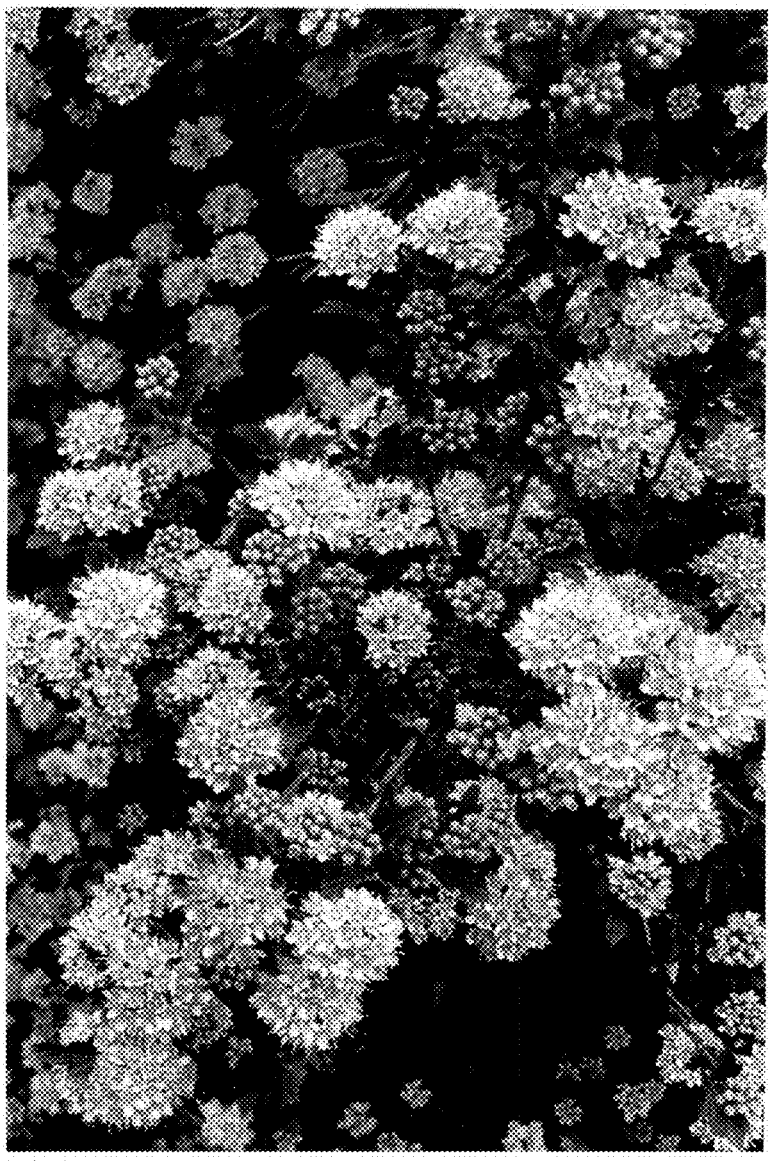
FIG. 3 illustrates dense floral coverage and darkening foliage in late May.
Figure 4:
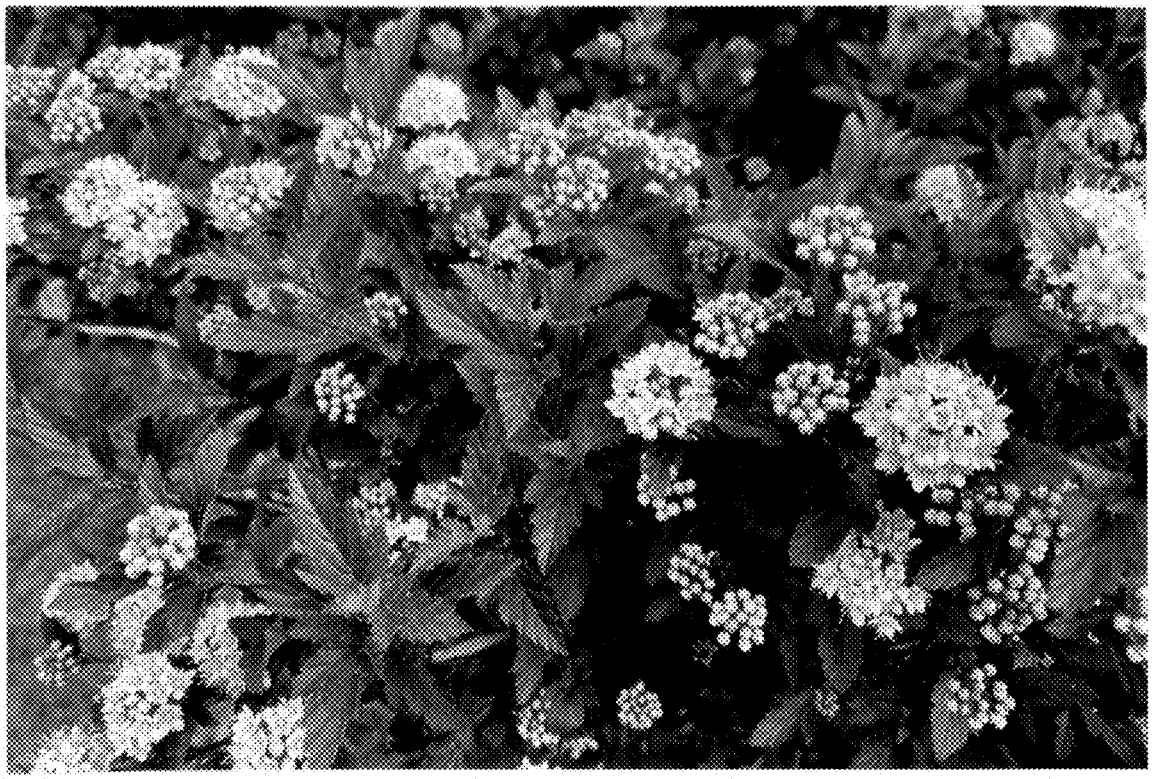
FIG. 4 illustrates flowers with colorful vegetative shoots in early June.
Figure 5:
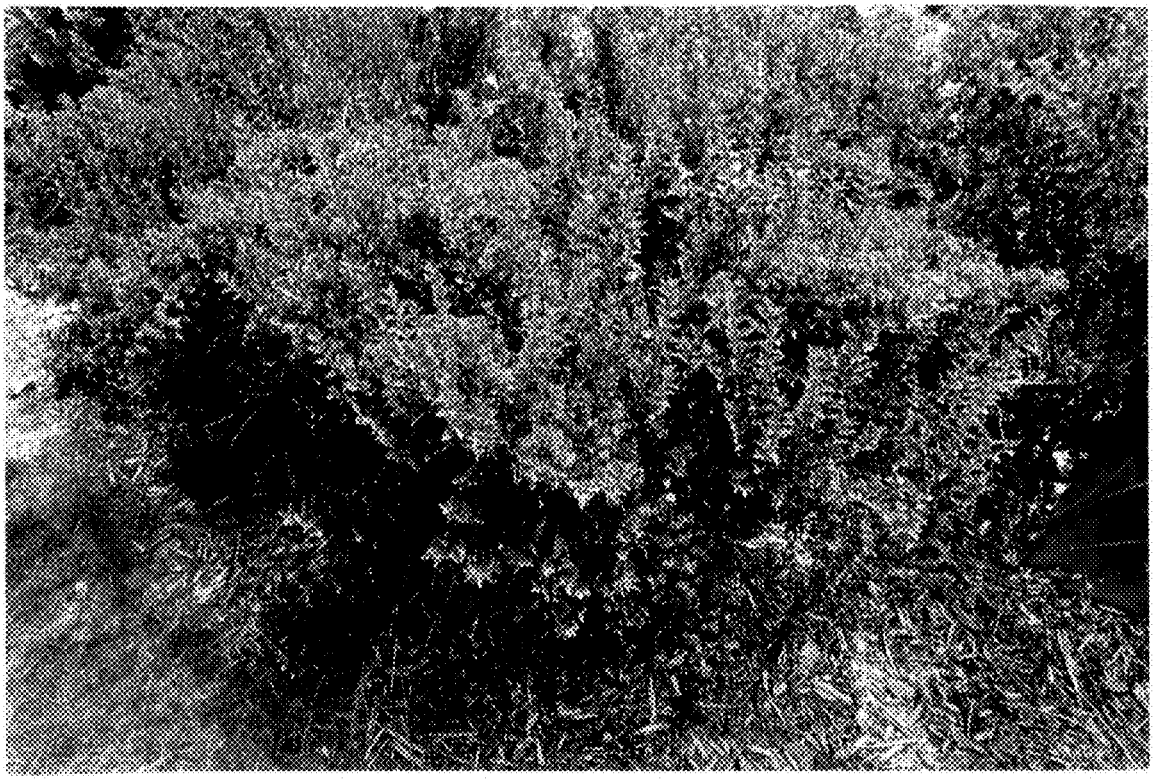
FIG. 5 illustrates the overall plant in late June after the first bloom.
Figure 6:
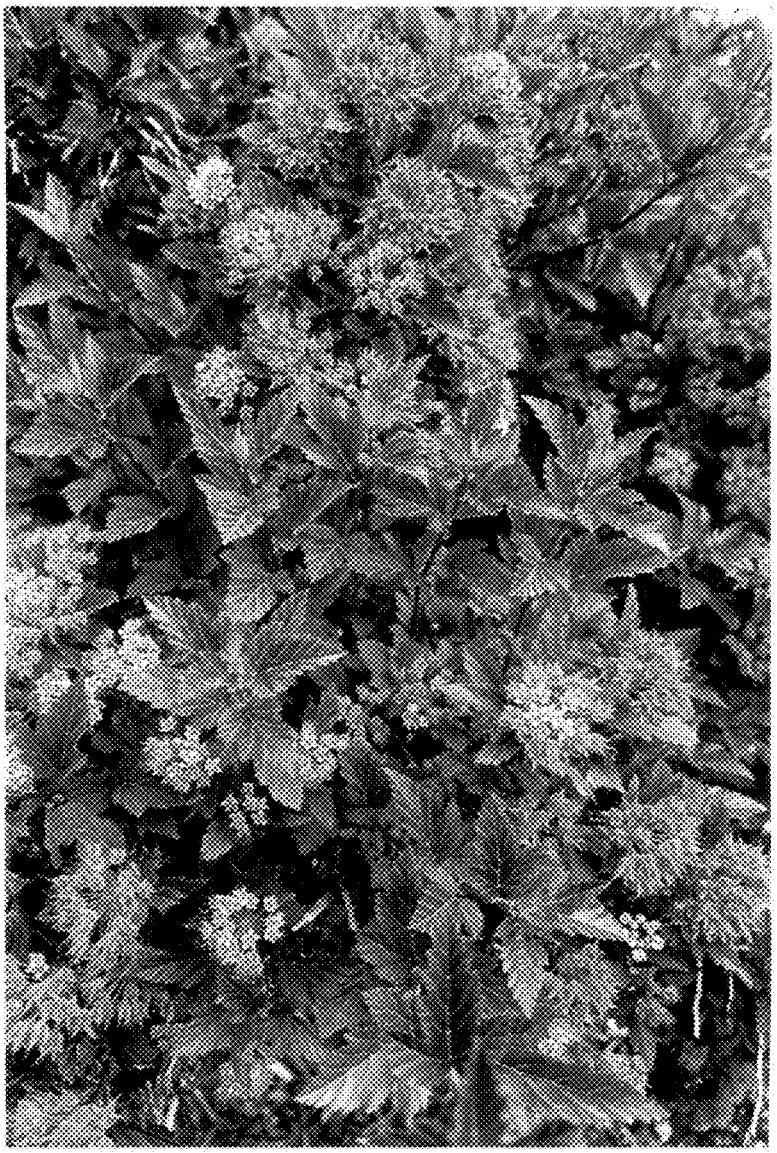
FIG. 6 illustrates colorful, developing fruit in late June.
Figure 7:
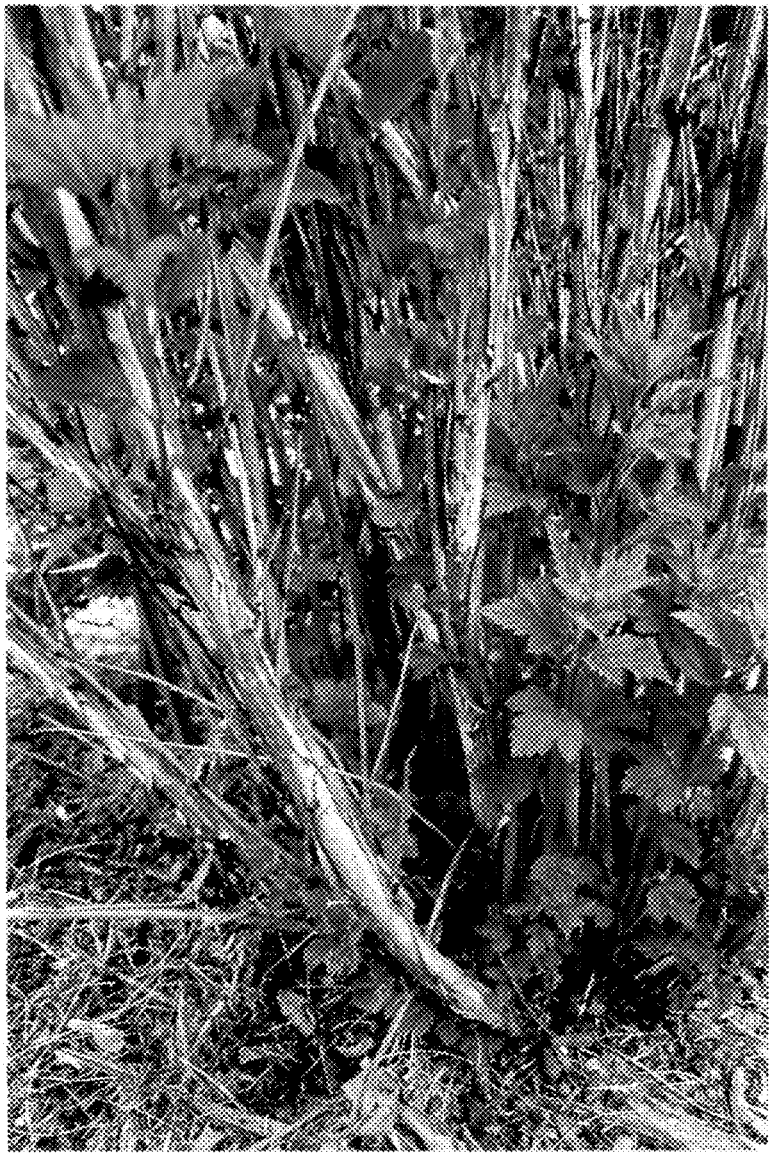
FIG. 7 illustrates exfoliating bark at the base of the plant in late June.
Figure 8:
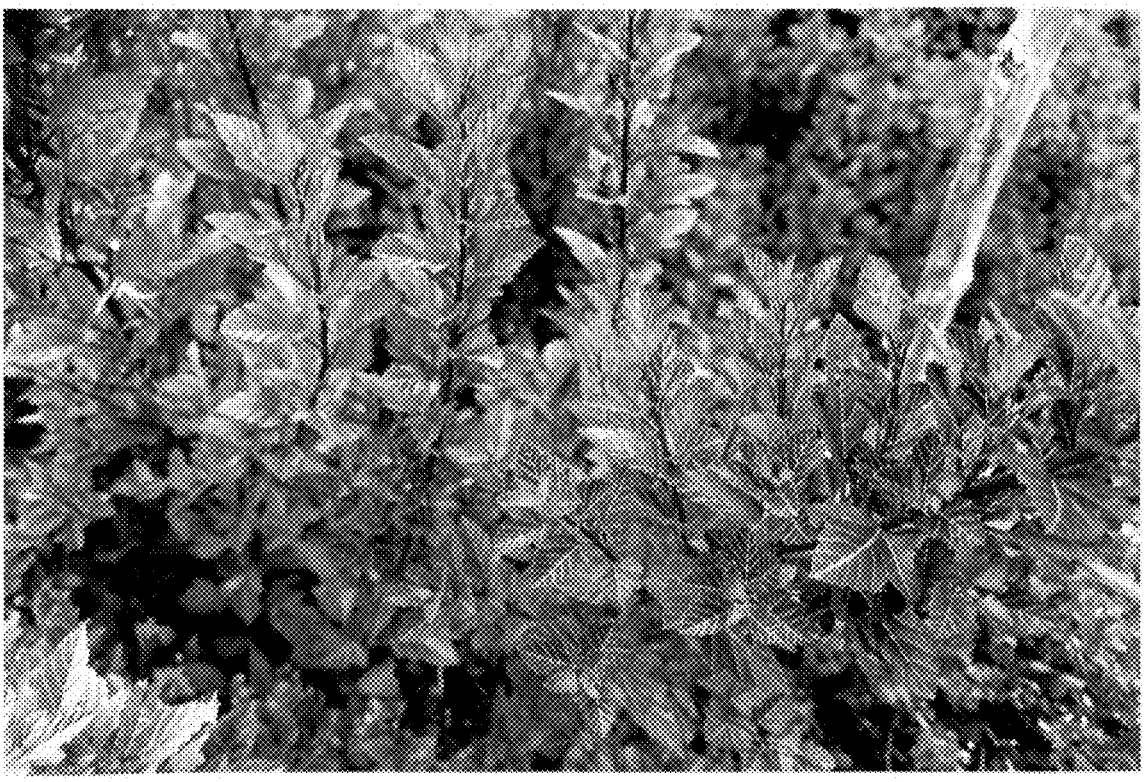
FIG. 8 illustrates natural branching from axillary buds on a current-season stem without pruning in early July.
Figure 9:
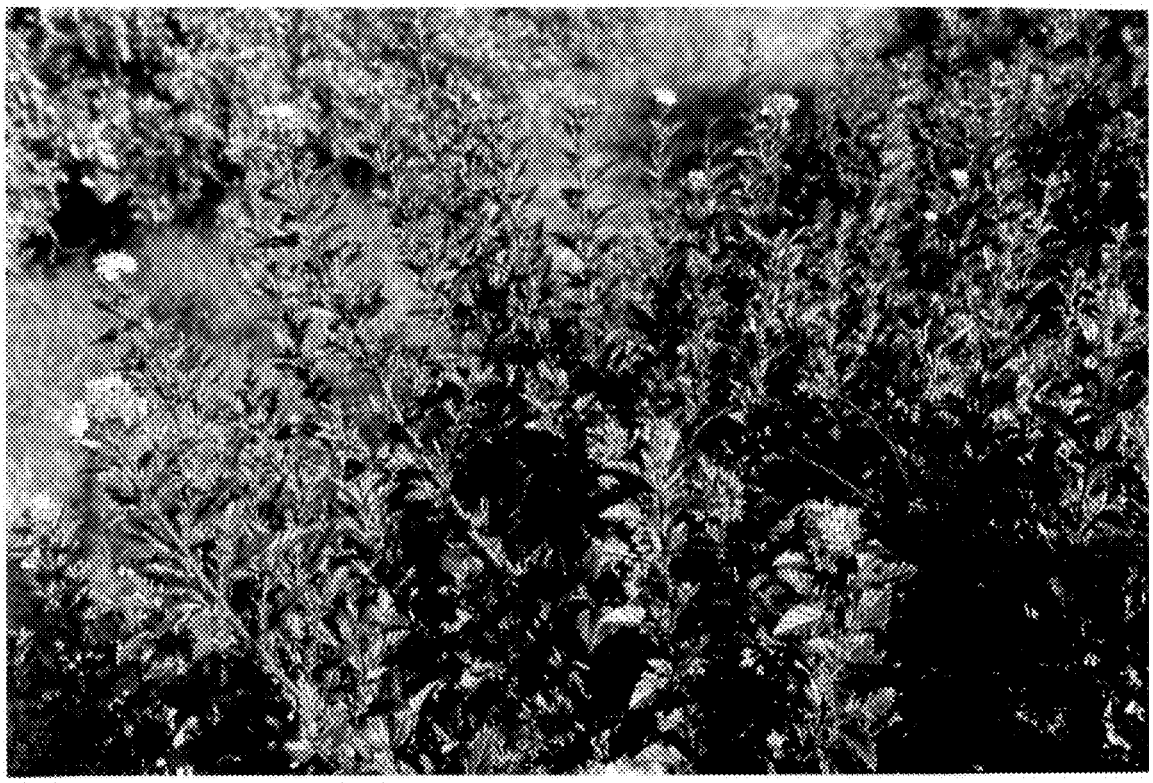
FIG. 9 illustrates vigorous stems terminating in inflorescences in early August.

The following is a detailed description of 'Auntie B', a new *Physocarpus opulifolius* cultivar, with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of the ortet during its sixth growing season in 2022 in a garden bed in River Falls, Wisc.

Classification:

*Botanical.*—*Physocarpus opulifolius* 'Auntie B'.

*Common names of the species.*—Ninebark, common ninebark, Atlantic ninebark, and Eastern ninebark.

*Commercial.*—Deciduous shrub.

Parentage:

*Origin.*—Seedling of 'ZLEBic5' as a maternal parent crossed with a full sibling of 'ZLEBic5' as the male parent.

General description:

*Plant habit.*—Upright, mounded, and compact.

*Plant size.*—1.0 m in overall height and width.

*Growth habit.*—Vigorous and dense with abundant branching.

*Blooming period.*—About 21 days from early to late June for the primary spring bloom display (short branches that terminate in inflorescences from vernalized, overwintered buds). Plants have reliable rebloom coming from terminals of vigorous new stems from late July into September.

*Hardiness.*—Cold hardy to at least USDA Zone 4.

*Root description.*—Fibrous and vigorous.

*Diseases and pest resistance.*—'Auntie B' has shown well above average resistance to powdery mildew with other ninebark genotypes heavily infected with powdery mildew growing adjacent to it. There are multiple species of fungi that cause powdery mildew on ninebark (*Phyllactinia guttata, Podosphaera aphanis* var. *physocarpi*, and *Podosphaera macularis*), and it is unclear which species were infecting it and the adjacent, much more susceptible ninebark genotypes.

*Cultural requirements.*—'Auntie B' does well in full to partial sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in the greenhouse without supplemental lighting for cuttings to typically form visible roots.

*Time required to obtain a well-rooted cutting.*—It takes about 6 to 7 weeks to produce a well-rooted cutting in a 2-inch container.

Branch description:

*Branch color.*—The background color of current season stems is Yellow-Green Group N144D and in sun it has a Greyed-Red Group 178B overlay. The most mature stems on a six-year-old plant had a mixture of colors on the exfoliating bark; color was primarily Greyed-Orange Group 165C, but there were also areas of Greyed-Orange Group 165B, Greyed-Orange Group 165C, Greyed-Orange Group 165D, and Orange-White Group 158A.

*Branch size.*—Branches produced during the current season of growth ranged from approximately 10-60 cm in length and 1-4 mm in width. The oldest branches on a six-year plant were up to 1.5 cm in diameter at the base of the plant.

*Branch surface.*—Young stems: Glabrous with a slight sheen. Older stems: Exfoliating bark layers that are somewhat dull and no longer have a sheen.

*Internode length.*—1.0-2.0 cm.

*Branch habit.*—Vigorous current season's stems typically produce new stems from axillary buds without pruning. Most vigorous growing stems terminate in a second flush of flowers by mid to late summer (late July through September) and this stimulates additional axillary buds on current season's growth to develop into shoots. The angle between the new stems arising from axillary buds and the stem from which they originated is typically 15-50°.

Foliage description:

*Overall leaf size.*—Leaf length is 3.5-5.5 cm and leaf width is 2.0-3.0 cm.

*Leaf division.*—Simple.

*Leaf attachment.*—Petiolate.

*Leaf arrangement.*—Alternate.

*Leaf number.*—It varies, but an actively growing branch can easily produce 30-60 leaves in a growing season.

*Leaf blade shape.*—Ovate in overall leaf blade outline with three prominent lobes.

*Leaf blade base.*—Rounded.

*Leaf blade apex.*—Acute to cuneate.

*Leaf blade venation.*—Primary venation is palmate with three principal veins. The principal veins diverge at the juncture of the leaf blade and petiole and continue with one principle vein through the middle of each of the three lobes. Secondary venation off the three principal veins is pinnate.

*Leaf blade margin.*—The three primary lobes have secondary lobes or serrations. The margin on the three primary lobes is best described as doubly serrate. The serrations extend out from the edge of the main leaf blade about 1.0-1.5 mm and there is typically between 3.0-4.0 mm between the tips of primary serrations and 1.0-2.0 mm between the tips of secondary serrations.

*Leaf blade surface.*—Glabrous on upper and lower surfaces.

*Leaf blade size.*—The leaf blade is approximately 2.75-3.25 cm long and 2.0-3.0 cm wide.

*Leaf blade color.*—Young emerging leaf blades on both surfaces are Yellow-Green Group 150A and have Greyed-Orange Group 176B along the margins. Young recently expanded leaf blades are closest to Greyed-Purple Group 187A on the upper surface and Yellow-Green Group 146C on the lower surface, except the veins on the lower surface are Yellow-Green Group 144C. Mature leaves are Green Group NN137A on the upper surface and Yellow-Green Group 144A throughout the lower surface, except the veins on the lower surface are Yellow-Green Group 144C.

*Petiole size.*—About 1.0-2.0 cm in length and about 1.0 mm in width.

*Petiole shape.*—Sulcate. The petiole is generally round except for a longitudinal furrow running the length of the upper surface.

*Petiole color.*—Greyed-Red Group 178B on the upper side and Yellow-Green Group 144C on the lower surface.

*Petiole texture.*—Glabrous.

*Stipule number.*—There are two stipules at each node with one on each side of the leaf petiole.

*Stipule size.*—2.0-3.0 mm long and 1.25 mm wide.

*Stipule shape.*—Generally lanceolate.

*Stipule color.*—Yellow-Green Group 144C with Greyed-Purple Group 183B highlights on the upper and lower surfaces.

Flower description:

*Inflorescence type.*—A corymb with 12-25 rotate flowers arranged in a hemisphere.

*Inflorescence size.*—Typically 1.5-2.0 cm in height and width.

*Inflorescence lastingness.*—The corymb has open flowers typically for up to 21 days with each individual flower open for approximately 3 days.

*Flower bud shape.*—Elliptic.

*Flower bud size and proportions.*—2.0-2.5 mm in length and 2.0 mm in width. The receptacle of the bud accounts for about half of the proximal end and the calyx accounts for about half of the distal end of an unopened flower bud.

*Flower bud color.*—The overall color of the unopened buds can best be described as Yellow-Green Group 144C with highlights or an overlay of Orange-Red Group N34C.

*Flower size when fully open.*—4.5-5.5 mm in diameter and 2.0-3.0 mm in depth (not including pedicel).

*Flower symmetry.*—Actinomorphic.

*Flower fragrance.*—Slight and sweet.

*Petal number.*—5.

*Petal size.*—2.25-2.50 mm in length and 2.0 mm in width.

*Petal shape.*—Elliptic to obovate.

*Petal color.*—As the flowers open, the lower petal surface as the sepals separate is Red-Purple Group 62A. Expanding petals are Greyed-Purple Group 186D on the upper surface and White Group N155B on the lower surface. Fully expanded petals are White Group N155B on both the upper and lower surfaces. Aging petals are typically White Group N155D right before petal drop.

*Sepal number.*—5.

*Sepal size.*—Length is 2.0 mm and width is 1.0-1.25 mm.

*Sepal shape.*—Deltoid.

*Sepal color.*—Yellow-Green Group N144C with an overlay of Orange-Red Group N34C.

*Sepal texture.*—Hoary on both surfaces.

*Pedicel size.*—The length ranges from about 1.0 cm for the flowers coming from the proximal or lower end of the corymb to about 0.5 cm for the flowers nearest the terminal or center of the corymb. Pedicels are round in cross section and are about 0.5-0.75 mm in diameter.

*Pedicel color.*—Yellow-Green Group 144C with highlights of Orange Red Group N34C. This color is the result of a green base color overlaid with red.

*Pedicel and receptacle texture.*—Glabrous.

*Subtending bract size.*—There is a subtending bract where each pedicel meets the peduncle of the corymb. The subtending bract is 2.0-3.0 mm long and 1.0 mm wide below where the pedicels attach at the proximal end of the corymb to 1.0-2.5 mm long and 0.75-1.0 mm wide under the more distal pedicels at the terminal or top of the corymb.

*Subtending bract shape.*—Elliptic to obovate with typically 3-5 very small and irregular serrations.

*Subtending bract color.*—Yellow-Green Group 144C with an overlay of Orange-Red Group N34C.

Gynoecium:

*Pistil number per flower.*—Typically there are 4, but sometimes 3.

*Stigma shape.*—Globular.

*Stigma size.*—0.25 mm in height and width.

*Stigma color.*—Yellow Green Group 150C.

*Style shape.*—Linear.

*Style size.*—About 3.0-4.0 mm long and 0.2 mm wide.

*Style color.*—Yellow-Green Group 150D.

*Ovary shape.*—Elliptic.

*Ovary size.*—About 1.5-2.0 mm in height and 0.75 mm in width.

*Ovary color.*—Yellow Green Group 145D.

Androecium:

*Stamen number per flower.*—Approximately 25.

*Anther shape.*—Elliptic to round.

*Anther size.*—About 0.3-0.4 mm in height and width.

*Anther color.*—Black Group 202A.

*Pollen color.*—White Group NN155B.

*Pollen abundance.*—Moderate.

*Filament shape.*—Linear.

*Filament size.*—1.0-2.0 mm long and 0.1-0.2 mm wide.

*Filament color.*—White Group NN155C.

Fruit and seeds:

*Fruit.*—There are typically three or four firm-walled follicles that form per flower. Follicles split along both sides of the seam, but split more readily along the inner or adaxial seam. Follicles are elongated and generally ovate in shape with acuminate tips. They are up to 5.0 mm long and approximately 2.0 mm wide at their widest point. They range in color from Greyed-Purple Group 183C in full sun to Greyed-Green Group 193A in more shade. Once mature, follicles dry and turn Greyed-Orange Group 165A.

*Seeds per follicle.*—There are typically 1-2 seeds per follicle.

*Seed shape.*—Ovate.

*Seed size.*—Generally 1.5 mm long and 1.25 mm wide.

*Seed color.*—Mature seed color is between Greyed-Orange Group 164C and Greyed-Orange Group 165D.

Winter hardiness: Acclimated plants of 'Auntie B' have displayed strong stem survival (complete survival to minor tip dieback) in United States Department of Agriculture cold hardiness zone 4 in River Falls, Wisc. without insulation.

I claim:

1. A new and distinct cultivar of *Physocarpus opulifolius* plant named 'Auntie B' substantially as herein shown and described, characterized particularly by an upright, mounded, dense plant habit; compact overall plant size; strong branching characteristics; small orange-red emerging foliage that matures to purple; short internode length; resistance to powdery mildew; corymbs of small blush-white flowers that are produced in late spring into early summer and reliably and abundantly again on vigorous current season stem terminals from mid-summer into fall; coral-pink to red follicle color when in full sun for about a month after fertilization; and ability to root and grow vigorously from softwood and semi-hardwood stem cuttings.

* * * * *